United States Patent [19]

Zengel et al.

[11] 4,071,555

[45] Jan. 31, 1978

[54] BENZENE-1,3,5-TRIS-ACETOXIME AND THE PROCESS FOR MAKING PHLOROGLUCINOL THEREWITH

[75] Inventors: Hans Zengel, Kleinwallstradt; Manfred Bergfeld, Erlenbach, Main, both of Germany

[73] Assignee: Akzona Incorporated, Asheville, N.C.

[21] Appl. No.: 796,109

[22] Filed: May 12, 1977

[30] Foreign Application Priority Data

May 14, 1976 Germany .............................. 2621431

[51] Int. Cl.$^2$ ............................................ C07C 131/00
[52] U.S. Cl. ............................ 260/566 A; 260/621 M
[58] Field of Search ..................................... 260/566 A

[56] References Cited

PUBLICATIONS

Chemical Abstracts, vol. 72, column 132,312(z), (1970).

*Primary Examiner*—Gerald A. Schwartz
*Attorney, Agent, or Firm*—Francis W. Young; Robert F. Green

[57] ABSTRACT

Phloroglucinol may be produced by converting s-triacetyl benzene to benzene-1,3,5-tris-acetoxime which is a novel compound. Said acetoxime is subjected to a Beckmann rearrangement and the resulting mixture subsequently hydrolyzed to produce phloroglucinol.

1 Claim, No Drawings

BENZENE-1,3,5-TRIS-ACETOXIME AND THE PROCESS FOR MAKING PHLOROGLUCINOL THEREWITH

BACKGROUND OF THE INVENTION

This invention relates to a process for making phloroglucinal and, in particular, a process for making phloroglucinol via a novel intermediate, namely benzene-1,3,5-tris-acetoxime.

Several processes for making phloroglucinol are already known. In particular, the reduction of 1,3,5-trinitrobenzene to 1,3,5-triaminobenzene and its subsequent hydrolysis to form phloroglucinol is industrially important. According to older processes, the reduction step may be accomplished by utilizing tin in hydrochloric solution (Weidel and Pollak, Monatsh. 21, 15, (1900); Hepp, Ann. 215, 348; Organic Synthesis Coll. Vol. I, 444 (1932); U.S. Pat. No. 2,461,498), or with hydrogen and Raney nickel in an organic solvent, such as ethyl acetate (German Patent No. 813,709; Gill et al., J. Chem. Soc., 1753 (1949); British Patent No. 1,106,088). A reducing agent suitable for the large-scale industrial reduction of the trinitrobenzene is iron/hydrochloric acid (U.S. Pat. No. 2,614,126; Kastens, Ind. and Engin. Chem. 42, 402 (1950); British Patent No. 1,022,733). Platinum, palladium and rhodium catalysts have also been proposed for the reduction of trinitrobenzene (French Patent No. 1,289,647; Desseigne, Mem. Poudres 44, 325 (1962). In such a synthesis, instead of starting with 1,3,5-trinitrobenzene, one can also start with 2,4,6-trinitrobenzoic acid, which on a large scale is obtainable through the oxidation of trinitrotoluene with sodium dichromate in sulfuric acid (Kastens, l.c.), since the 2,4,6-triaminobenzoic acid formed in the reduction either decarboxylates immediately to triaminobenzene, or is converted to phloroglucinol during the subsequent hydrolysis (British Patent Nos. 1,022,733; 1,106,088; 1,274,551). Furthermore, it is known to start with 5-nitro-1,3-diaminobenzene instead of trinitrobenzene (British Patent No. 1,012,782. The hydrolysis of the triamine to phloroglucinol is customarily carried out in a mineral acid solution (Flesch, Monatsh. 18, 755 (1897); German Patent No. 102,358, or, according to a more recent process, in the presence of copper and/or its salts as catalysts (German Patent No. 1,195,327).

According to a process likewise of interest from an industrial viewpoint, one may obtain phloroglucinol by oxidizing 1,3,5-triisopropyl benzene, separating the trihydroperoxide from the resulting mixture of mono-, di- and trihydroperoxides, and subjecting it subsequently to ketone splitting (British Patent No. 751,598; German Patent No. 12,239; Seidel et al., Journ. prakt. Chemie 275, 278 (1956). It is also possible to convert triisopropyl benzene directly to phloroglucinol triacetate through oxidation with oxygen in acetic anhydride, followed by hydrolysis with alcoholic sodium hydroxide to form phloroglucinol. One may also start with m-isopropyl resorcinol, which is esterified with acetic anhydride; the resulting m-isopropyl resorcinol diacetate is then oxidized to hydroperoxide and the latter is finally converted to phloroglucinol with acid (U.S. Pat. No. 3,028,410). Phloroglucinol may also be obtained, if resorcinol (Barth and Schreder, Ber. 12, 503, (1879) in 2-,4-,5-,3,5- or 2,4-position, resorcinol substituted by chlorine or bromine (German Patent No. 2,231,005), or 1,3,5-benzene trisulfonic acid (U.S. Pat. No. 2,773,908) are melted with excess alkali hydroxide.

In addition to the listed benzene derivatives, mention has also been made of hexahydroxybenzene, picryl chloride, tetrachloro- and tetrabromobenzene, as well as tribromobenzene, as initial materials for phloroglucinol synthesis. Hexahydroxybenzene may be hydrated with platinum oxide in an aqueous medium (Kuhn et al., Ann. 565, 1 (1949), picryl chloride may be reduced with tin and hydrochloric acid, or electrolytically, and the 1,3,5-triaminobenzene, or 2,4,6-triamino-1-chlorobenzene obtained thereby may then be hydrolyzed (Heertjes, Recueil 78, 452 (1959).

The above-mentioned tetrahalobenzenes may be subjected to ammonolysis in the presence of a copper catalyst and the intermediary triamine may be hydrolyzed in the reaction mixture without a preceding separation (U.S. Pat. No. 3,230,266). Tribromobenzene may be converted to 1,3,5-trimethoxybenzene with sodium methanolate and catalytic quantities of copper iodide in methanol/dimethyl formamide as a solvent, and also may be subsequently subjected to hydrolysis (McKillop et al., Synthetic Communications 4 (1) 43,35 (1974).

Furthermore, there is also a known phloroglucinol synthesis based on diethyl malonate. When subjected to treatment with metallic sodium, the malonic diethyl ester may condense with itself to form the trisodium salt of phloroglucinol dicarboxylic diethyl ester and this intermediate product may then be subjected to alkaline hydrolysis and decarboxylation (v. Baeyer, Ber. 18, 3454 (1885); Willstaetter, Ber. 32, 1272 (1899); Leuchs, Ber. 41, 3172 (1908); Komninos, Bull. Soc. Chem. Fr. 23, 449 (1918). Such a synthesis has been improved to the extent that the formation of the sodium malonic diethyl ester and the trisodium salt of phloroglucinol dicarboxylic diethyl ester may be performed in a single operation by means of boiling in an inert, high-boiling solvent, preferably dekalin (German Patent No. 29,998).

From the above-mentioned processes, apparently only the process based upon 2,4,6-trinitrobenzoic acid has been utilized commercially. However, such a process has several serious drawbacks. 2,4,6-trinitrobenzoic acid may be prepared by oxidizing trinitrotoluene, which is explosive, thus rendering such a process dangerous. In addition, the total yield, measured on the basis of 2,4,6-trinitrobenzene, of phloroglucinol produced via the intermediates of trinitrobenzene and triaminobenzene, is low. Such a process is also disadvantageous because the waste water formed during the oxidation and reduction is strongly acid and contains the heavy metals chromium and iron, and must therefore be treated.

A primary object of the present invention is to provide a process which is suitable for the commercial manufacture of phloroglucinol, but does not suffer from the disadvantages of the presently utilized industrial processes.

SUMMARY OF THE INVENTION

It has now been discovered that phloroglucinol may be produced by a process in which s-triacetyl benzene is converted to benzene-1,3,5-tris-acetoxime, which is then subjected to a Beckmann rearrangement, followed by an acid hydrolyzation of the mixture of substances obtained thereby.

DESCRIPTION OF THE PREFERRED EMBODIMENTS s-Triacetyl benzene is an easily accessible initial compound. It may be formed with practically quantitative yield by the acidification of acetoacetic aldehyde-acetal and may be formed in many reactions in which acetoacetic aldehyde occurs in an intermediary manner. A number of the last-mentioned processes are carried out on an industrial scale. For example, the desired initial compounds are obtained through condensation of acetone with formic acid esters, or of orthoacetic ester with methylvinyl ether, through the addition of acetyl chloride to acetylene, or of two equivalents of methanol to diacetylene, or through the oxidation of crotonaldehyde with air on palladium or platinum salts at room temperature.

In the first aspect of the present invention, s-triacetyl benzene is reacted with hydroxylamine or hydroxylamine hydrochloride to form the novel compound benzene-1,3,5-tris-acetoxime which has the formula:

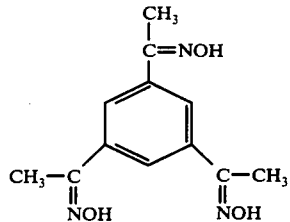

The foregoing compound has a faintly beige color, is finely crystalline, melts at 242°–245° C, dissolves well in dimethyl formamide, dimethyl acetamide, dimethyl sulfoxide, hexamethyl phosphoric acid triamide, dissolves fairly well in methanol, ethanol acetone and glycol, is soluble with difficulty in toluene, benzene, ether and methylene chloride, and is insoluble in petroleum ether and water.

Benzene-1,3,5-tris-acetoxime is not readily prepared by using customary oxime synthesis techniques. For example, the results obtained by converting the carbonyl compound with free hydroxylamine in boiling ethanol, or with hydroxylamine hydrochloride and sodium acetate in an aqueous medium, were not commercially satisfactory. However, preparation of the benzene-1,3,5-tris-acetoxime with high yield is accomplished by converting s-triacetyl benzene with hydroxylamine hydrochloride in the presence of a metal hydroxide in ethylene glycol, diethylene glycol, propanediol, or butanediol at temperatures from about 70° to about 170° C. In principle, higher reaction temperatures are operable, but are usually economically undesirable.

Preferably, the hydroxylamine hydrochloride is used in substantially stoichiometric quantities, about 3 moles of hydroxylamine hydrochloride are utilized per mole of s-triacetyl benzene. A slight excess of either reaction constituent may be used without detriment. Although any metal hydroxide may be utilized, the metal hydroxides which are especially preferred are the alkali and alkaline earth hydroxides; most preferably, sodium hydroxide. The hydroxide should be used in substantially metric quantities, about 3 moles of sodium hydroxide per mole of s-triacetyl benzene. Of course, a slight excess or deficiency may be utilized.

Ethylene glycol, diethylene glycol, butanediol-1,4, as well as propanediol are suitable solvents. However, other diols which are solvents for the alkali or alkaline earth hydroxide, as well as glycerin, may also be utilized. Preferably, ethylene glycol, diethylene glycol and butanediol-1,4 are used as solvents. Conversion to the oxime is preferably carried out at temperatures from about 90° to about 150° C. The reaction is allowed to proceed for a length of time sufficient to form a substantial amount of benzene-1,3,5-tris-acetoxime. Reaction times are usually within a range from about 30 minutes to about 10 hours. At this stage of the process the yield is more than 90% of theoretical.

In the second aspect of the present invention, benzene-1,3,5-tris-acetoxime is subjected to a Beckman rearrangement. As is known, in a Beckmann rearrangement there occurs the rearrangement of ketoximes under the influence of acid chlorides or concentrated acids, to form acid amides (Houben-Weyl, Methoden der Organischen Chemie/Methods of Organic Chemistry/, Georg Thieme Publishing House, Stuttgard, Vol VIII, (1952), p. 669, Vol X/4 (1968), p. 230. Vol. XI/1 (1957) p. 892 and Vol XI/2 (1958) p. 550; L. G. Donaruma and W./Z. Heldt, Org. Reactions 11, 1–156 (1960). In the case of the Beckmann rearrangement in general, and particularly with respect to the benzene-1,3,5-tris-acetoxime pursuant to the invention, previously known methods do not satisfactorily produce the desired product. For example, if sulfuric acid, oleum, or polyphosphoric acid are used, heating to the temperature required for the rearrangement will mainly produce a gummy reaction product and low-molecular weight degradation products. If it is attempted to carry out the reaction in a so-called Beckmann mixture, a mixture of glacial acetic acid/acetic anhydride, one obtains after heating for 12 hours with reflux merely a high yield of the undesirable tris-acetylated ketoxime, but no rearrangement product. It was not possible to find any significant amount of product after boiling for 48 hours with reflux in ether and in the presence of excess phosphorus pentachloride, a mixture which, because of the formation of an especially favorable waste group, is particularly recommended for difficult Beckmann rearrangements. Even after 24 hours of boiling in trifluoroacetic acid there was no noticeable reaction.

By contrast, practice of the Beckmann rearrangement of benzene-1,3,5-tris-acetoxime in trifluoroacetic acid at temperatures above 80° under its inherent partial pressure, is surprisingly successful. Preferably, the conversion in trifluoroacetic acid is carried out in the range from about 80° to about 150° C, although higher temperatures are operable. The reaction is allowed to proceed for a length of time sufficient to allow substantially all of the acetoxime to undergo the rearrangement. Under such conditions, the rearrangement is nearly quantitative after about 45 minutes. After removing the excess trifluoroacetic acid, as by distillation, a product mixture is obtained from the clear, brown solution, which contains 1,3,5-triaminobenzene and 1,3,5-triacetamidobenzene as main constituents. The yield of these two products amounts to more than 85% of theoretical, based on benzene-1,3,5-tris-acetoxime. In addition to the main reaction products, the reaction mixture always contains small quantitities of 1-acetyl-bis-acetamidobenzene formed through partial hydrolysis of the benzene-1,3,5-tris-acetoxime, as well as the secondary products 1-trifluoracetamido-3,5-bis-acetamidobenzene and 1-acetyl-3-acetamido-5-trifluoracetamidobenzene, formed through re-acetylation with trifluoroacetic acid or hydrolysis of the latter. On the other hand, it was not possible to detect any compounds which, in the event of migration of the methyl group, would occur in the course of Beckmann rearrangement in place of the phenyl nucleus, such as benzoic, isophthalic or trimesic acid-N-methylamide. The high level of selectivity possible with the Beckmann rearrangement utilized in the process of the present invention is especially surprising, particularly in the case of polyfunctional ketones, since there typically is a formation of cleavage products which are caused by a number of reactions competing with the Beckmann rearrangement.

In the last aspect of the present invention, the reaction mixture obtained in the Beckmann rearrangement of the benzene-1,3,5-tris-acetoxime is made substantially free of excess trifluoroacetic acid and subjected to acid hydrolysis. Any aqueous acid is suitable for the hydrolysis, aqueous hydrochloric acid or sulfuric acid being preferred. The hydrolysis is preferably carried out at temperatures from about 100° to about 200° C, although lower or higher temperatures may be utilized, and at the corresponding inherent partial pressures. The reaction is carried out until the hydrolysis reaction is substantially complete, usually within from about 5 to about 24 hours. Preferably, the hydrolysis is carried out with about 1.1 to about 1.5 times the molar quantity of mineral acid, with respect to the benzene-1,3,5,-tris-acetoxime used, at temperatures from about 130° to about 180° C.

The reaction mixture contains the desired phloroglucinol, acetic acid and ammonium chloride, as well as small quantities of phloroglucide, in a typical yield of 85% based on benzene-1,3,5-tris-acetoxime, and of more than 90% based on the benzene-1,3,5-triamino derivative. In the industrial preparation of phloroglucinol according to the process of the present invention, the phloroglucide, which is difficult to dissolve, may be removed from the hot hydrolysis mixture by means of filtration. The phloroglucinol then crystallizes out when the filtrate cools and may be separated by filtration or centrifuging.

The process pursuant to the invention is especially suitable for the industrial-scale preparation of phloroglucinol. In contrast to known processes, no use is made of an explosive initial material. In addition, high yields are obtained in all stages of the process, so that the total yield is higher than in the known processes. Also, waste water which is strongly acidic, or contains heavy metals, does not result from the present process, so that it is ecologically better suited than the known processes.

Phloroglucinol, as is well known, may be used as a developer in diazo printing, as a cross-linking, vulcanizing, stabilizing or anticorrosion agent, as well as a coupling component in the manufacture of numerous dyestuffs. In analytical chemistry it is used as reagent for aldehydes, pentoses, lignin, galactoses and other substances. Furthermore, it is required in the preparation of coumarines, flavonols and pharmaceutical materials. The process of the present invention is explained further by the following non-limiting examples.

Synthesis of Benzene-1,3,5-trisacetoxime

EXAMPLE 1

40 g of sodium hydroxide (1 mole), finely powdered, were first dissolved at elevated temperatures (40°-80° C), with vigorous stirring, in 1.5 liters of ethylene glycol contained in a 2 liter three-necked flask equipped with dropping funnel, reflux cooler and agitator and subsequently mixed with 69.5 g (1 mole) of hydroxylammonium chloride. After the hydroxylamine had been liberated, 61.2 g (300mmole) of triacetylbenzene were added in portions. The reaction mixture was subsequently heated to 120° C in the course of 15 minutes and maintained at this temperature for 5 hours with vigorous agitation. The result was a light-brown, clear solution, from which, after cooling, 80% of the theoretical yield of the formed benzene-1,3,5-trisacetoxime containing common salt impurities was separated. After concentration of the glycolic mother liquor and diluting of the formed residue with 500 ml of water, (separation of the concurrently precipitated NaCl) it was possible to obtain another 16% benzene-1,3,5-trisacetoxime. The crude benzene-1,3,5-trisacetoxime was subsequently recrystallized from 2 liters of aqueous ethanol. In so doing, it was possible to obtain 68.3 g (274mmoles) of pure benzene-1,3,5-trisacetoxime, corresponding to 91.3% of the theoretical yield in the form of fine, white needles with a melting point of 244° to 246° C.

EXAMPLE 2

Analogous to Example 1, 18.36 g (90mmole) of 1,3,5-triacetyl benzene were reacted with 19 g (273mmole) of hydroxylammonium chloride and 15.85 g (282mmole) of potassium hydroxide in a total of 400 ml of ethylene glycol. Execution of the reaction and processing were carried out analogous to Example 1. After cooling of the glycolic solution, the yield of crude benzene-1,3,5,-trisacetoxime was 85% of theoretical. It was possible to obtain another 12% of benzene-1,3,5,-trisacetoxime from the glycolic phase through concentration and dissolving of the formed potassium chloride with water. Purification of the two crude products was carried out by dissolving in a small amount of hot ethanol and precipitating the trisoxime with an adequate quantity of water. In this manner, 21 g (84.0mmole), corresponding to 93.5% of theoretical, of benzene-1,3,5-trisacetoxime in the form of white flakes with a melting point of 242° to 246° C were obtained.

In case of continuous operation, processing of the glycolic phase becomes unnecessary. Rather, the latter, with the benzene-1,3,5-trisacetoxime dissolved therein, is used directly for the preparation of the following batch.

EXAMPLE 3

Analogous to Example 2, 18.36 g (90mmole) of 1,3,5-triacetyl benzene were reacted with 19 g (273mmole) hydroxylammonium chloride and 15.85 g (282mmole) of potassium hydroxide in the glycolic mother liquor of Example 2. Execution of the reaction and processing were carried out analogous to Example 1. However, there was an increase in the yield of 85% of theoretical of benzene-1,3,5-trisacetoxime obtained in Example 2, to 92.5% of theoretical. Removal of the concurrently precipitated potassium chloride was again carried out through recrystallization from ethanol/water.

EXAMPLE 4

Analogous to Example 1, 5.6 g (100mmole) hydroxylammonium hydrochloride and 6.12 g (30mmole) 1,3,5-triacetyl benzene were reacted in 75 ml of butanediol-1,4. The reaction mixture was heated to 140° C in the course of 5 minutes and maintained at this temperature for 3 hours with vigorous agitation. A clear reaction solution formed after only a short time, from which about 50% of the formed benzene-1,3,5-trisacetoxime precipitated after cooling. After distilling off most of the solvent and subsequently dissolving the residue which was still moist with, butanediol with water, (removal of the formed potassium chloride) it was possible to obtain 6.76 g (27mmole), corresponding to 90.5% of theoretical, of benzene-1,3,5-trisacetoxime in crystalline form.

In a parallel experiment, in which ethanol was used as the solvent instead of butanediol-1,4, it was not possible to detect any benzene-1,3,5-trisacetoxime after a reflux duration of 24 hours under otherwise identical conditions.

Synthesis of 1,3,5-triacetaminobenzene

EXAMPLE 5

20 g (80.3mmole) of benzene-1,3,5-trisacetoxime were heated for 24 hours in 300 ml trifluoroacetic acid with vigorous agitation and reflux. It was not possible to detect any transformation.

An analogous batch was heated in a glass autoclave for 4 hours at 120° C under autogenous pressure. A clear, light brown solution was formed, of which a viscous mass was left after the solvent was distilled off. In order to free it of traces of adhering trifluoroacetic acid, the mass was boiled with 100 ml of ethanol. Fractional crystallization from ethanol/water produced 65.5% of theoretical of 1,3,5-trisacetamidobenzene and subsequent precipitation with HCl gas resulted in 19.8% of 1,3,5-triaminobenzene in the form of its HCl salt. By means of high-pressure liquid chromatography it was furthermore possible to detect in addition about 5% of 1-amino-3,5-bis-acetamidobenzene and 1,3bis-acetamido-5-trifluoracetamidobenzene, which may also be converted to phloroglucinol during subsequent hydrolysis. Thus, the degree of conversion of benzene-1,3,5-trisacetoxime to benzene-1,3,5-trisaminoderivatives hydrolyzable to phloroglucinol amounted to more than 90% of theoretical.

Rearrangement of Benzene-1,3,5-trisacetoxime and Hydrolysis of the Rearrangement Product to Phloroglucinol without Intermediate Isolation

EXAMPLE 6

19.1 g (76.7mmole) of benzene-1,3,5-trisacetoxime were suspended in 250 ml trifluoroacetic acid in a 500 ml glass autoclave equipped with a Teflon ® agitator and thermometer connection and heated to 125° C within 15 minutes with vigorous agitation. This resulted in a clear solution, which, in order to complete the reaction, was left at this temperature for another 40 minutes. Subsequently, the solvent (trifluoroacetic acid) was distilled off, the light brown residue subsequently mixed with 300 ml of a 1N-aqueous hydrochloric acid and decomposed for 20 hours with vigorous agitation at 175° to 180° C. Thereby, an inherent partial pressure of about 15 atmospheres gauge pressure was produced. The dark reaction solution was subsequently concentrated in a vacuum at 50° C and extracted with acetic ester, 8.3 g (67.mmole), corresponding to 87.5% of theoretical, of phloroglucinol were isolated from the acetic ester extract.

Depending upon the duration of the hydrolysis reaction, as well as upon the acid concentration used and the reaction temperature, the phloroglucinol is still contaminated with 3 to 7% phloroglucide. The latter, because it is difficult to dissolve in water, can very easily be separated from the phloroglucinol. Afterwards, during cooling, the phloroglucinol accumulates in crystalline form from the hot, aqueous filtrate and the product is very pure. If required, a completely colorless product can be obtained through recrystallization from water with an addition of activated carbon.

EXAMPLE 7

Analogous to Example 6, 20 g (80.3 mmole) of benzene-1,3,5-trisacetoxime in 275 ml trifluoroacetic acid were heated to 140° C for 50 minutes (closed system), whereupon the solvent was removed in a vaccum. The remaining brown crystal mass was then suspended in 350 ml of 0.75 N sulfuric acid with vigorous agitation and heated to 160°-170° C for 12 hours (corresponding to an inherent partial pressure of 10 to 14 atmospheres gauge pressure). A dark, clear solution was formed thereby, which was neutralized with soda and extracted with ether. In this manner it was possible to obtain 8.38 g (66mmole), corresponding to 82% of the theoretical yield of phloroglucinol, based on the charged benzene-1,3,5-trisacetoxime, from the ether extract. Contamination with phloroglucide amounted to 3 to 5% of theoretical. A simple removal of this contamination and simultaneous decoloration is possible through recrystallization with water and addition of activated carbon, as described in Example 6.

What is claimed is:

1. Benzene-1,3,5-tris-acetoxime.

* * * * *